United States Patent [19]

Tribble et al.

[11] Patent Number: 5,229,186

[45] Date of Patent: Jul. 20, 1993

[54] DEEP EMBOSSED PLASTIC FILM

[75] Inventors: James D. Tribble, Brazil; Alvin W. Gross, Terre Haute, both of Ind.

[73] Assignee: Tredegar Industries, Inc., Richmond, Va.

[21] Appl. No.: 726,870

[22] Filed: Jul. 8, 1991

[51] Int. Cl.$^5$ .................. B32B 3/00; A61F 13/15
[52] U.S. Cl. .................. 428/156; 428/141; 428/178; 428/212; 428/409; 428/338; 604/358; 604/367
[58] Field of Search ............ 428/156, 122, 141, 178, 428/212, 409, 500, 220, 338, 521; 51/410; 264/162, 284; 156/209, 244.25; 2/409; 604/358, 367, 393; D6/595, 608

[56] References Cited

U.S. PATENT DOCUMENTS

| | | | |
|---|---|---|---|
| Re. 23,910 | 12/1954 | Smith | 18/9 |
| 3,484,835 | 12/1969 | Trounstine | 161/130 |
| 3,849,050 | 11/1974 | Adams | 425/363 |
| 3,894,827 | 7/1975 | Raley | 425/365 |
| 3,911,187 | 10/1975 | Raley | 428/180 |
| 3,950,480 | 4/1976 | Adams | 264/284 |
| 3,957,414 | 5/1976 | Bussey, Jr. | 425/384 |
| 3,966,383 | 6/1976 | Bussey, Jr. | 425/388 |
| 4,157,237 | 6/1979 | Raley | 425/363 |
| 4,343,848 | 8/1982 | Leonard, Jr. | 428/156 |
| 4,376,147 | 3/1983 | Byrne | 428/167 |
| 4,436,520 | 3/1984 | Lipko | 428/121 |
| 4,518,643 | 5/1985 | Francis | 428/131 |
| 4,546,029 | 10/1985 | Cancio | 428/141 |

FOREIGN PATENT DOCUMENTS 63-66241  3/1988  Japan.
3-30934  2/1991  Japan.

OTHER PUBLICATIONS

Quilted Diaper and Sanitary Napkin Products, Johnson & Johnson Baby Products Co., Pienak, H. A., GB 2 100 130 A Corporate Author–Johnson & Johnson Language–English.

Improvement of Diaper Liners Made From Polyethylene Terephthalate Nonwoven Webs, No Author.

*Primary Examiner*—Donald J. Loney
*Attorney, Agent, or Firm*—Emch, Schaffer, Schaub & Porcello Co.

[57] ABSTRACT

A deep embossed thermoplastic film is disclosed. The film includes a plurality of macro cells. The macro cells are interconnected by lands extending between adjacent macro cells. The film also includes at least one plurality of micro depressions, whereby a pleasing appearance and a proper feel are imparted.

13 Claims, 3 Drawing Sheets

DEEP EMBOSSED PLASTIC FILM

BACKGROUND OF THE INVENTION

The present invention is directed to a deep embossed plastic film and more particularly to a plastic film having a plurality of deep embossed macro cells together with one or more pluralities of micro cells or depressions.

Embossed plastic films are known in the art and are used as a substitute for textiles. Embossed films may be used for many different purposes such as diaper liners, panty liners and sanitary napkins.

Examples of prior art films are disclosed in U.S. Pat. Nos. 3,911,187 and 4,518,643.

When used as a diaper liner or as a substitute for an apparel textile material, many of the prior art films did not have the aesthetic quality that a deep embossed film provides. In addition, many of the prior art films had a final gloss which was not appealing to the eye. Many of the prior art films did not have the tactile characteristics which gave an appealing "feel" quality to the final film product.

It is, therefore, the object of the present invention to provide an improved deep embossed plastic film which has the characteristics not found in prior art plastic films.

SUMMARY OF THE INVENTION

The present invention relates to a deep embossed plastic film. The deep embossed plastic film has a plurality of deep embossed macro cells. The macro cells are interconnected by lands extending between adjacent cells. The film also includes at least one plurality of micro cells or depressions. In other embodiments, at least two pluralities of micro cells or depressions are provided on the film.

DESCRIPTION OF THE PREFERRED EMBODIMENTS

Figure 1:
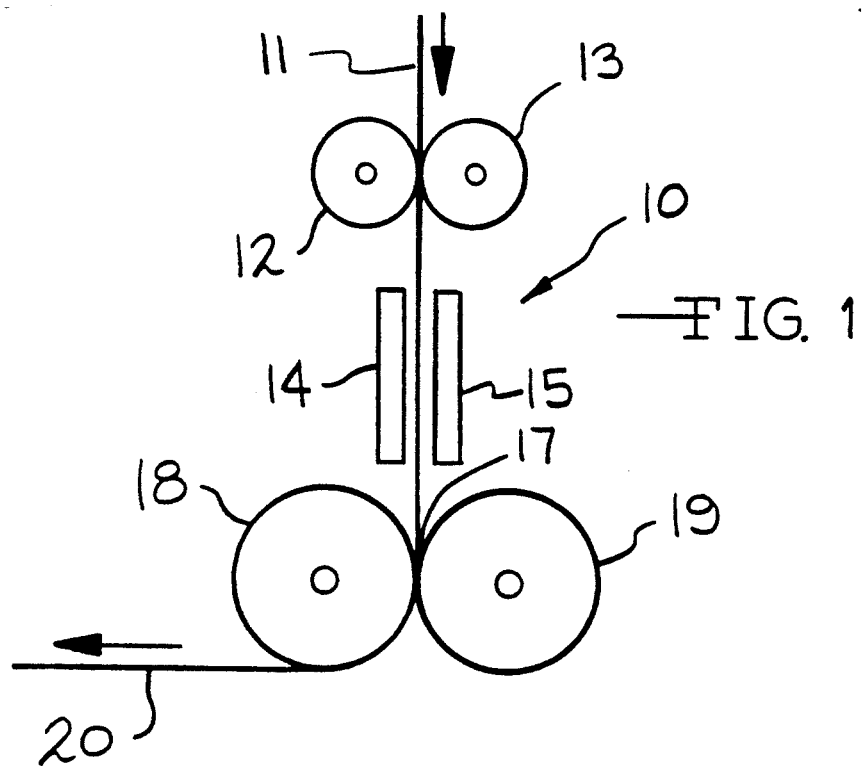
FIG. 1 is a diagrammatic elevational view of a typical apparatus for manufacturing a deep embossed plastic film, according to the present invention.

Referring to FIG. 1, an apparatus for producing a deep embossed plastic film, according to the present invention, is generally indicated by the reference number 10. A preformed, flat, longitudinally extending web of thermoplastic film 11 is fed through the nip of driven pull rods 12 and 13. The thermoplastic film 11 can be formed by either a cast process or a blown process, however, a blown process is normally preferable. The thermoplastic film 11 is generally a polyolefin film, such as polyethylene. However, the present invention is not limited to polyolefin films.

The film 11 passes downwardly between spaced apart opposed heaters 14 and 15. The heaters 14 and 15 raise the temperature of the film 11 above its softening point. The heat softened film 11 then passes into a nip 17 formed by a metal embossing roll 18 and a backup roll 19 covered with a outer layer of a resilient material, such as a rubber or rubber-like material. In the present embodiment, the embossed macro and micro patterns are imparted as the film 11 passes between the rolls 18 and 19 to generate a deep embossed thermoplastic film 20, according to the present invention.

Other types of polyolefin-type thermoplastic films include polypropylene; copolymers of polyolefins such as ethylene-vinyl acetate copolymers; or modified polyolefins polymers such as polyethylene or polypropylene modified with conventional fillers.

The thickness of the unembossed thermoplastic film 10 is normally between 0.5 mil and 6 mil with a preferable range between 0.5 mil and 3 mil. The unembossed thickness of the film 10 used to produce the deep embossed plastic film 20, shown in FIGS. 3–6, is 1 mil. For many applications, including diaper liners, 1 mil is a preferred thickness of the unembossed film 10.

Figure 3:
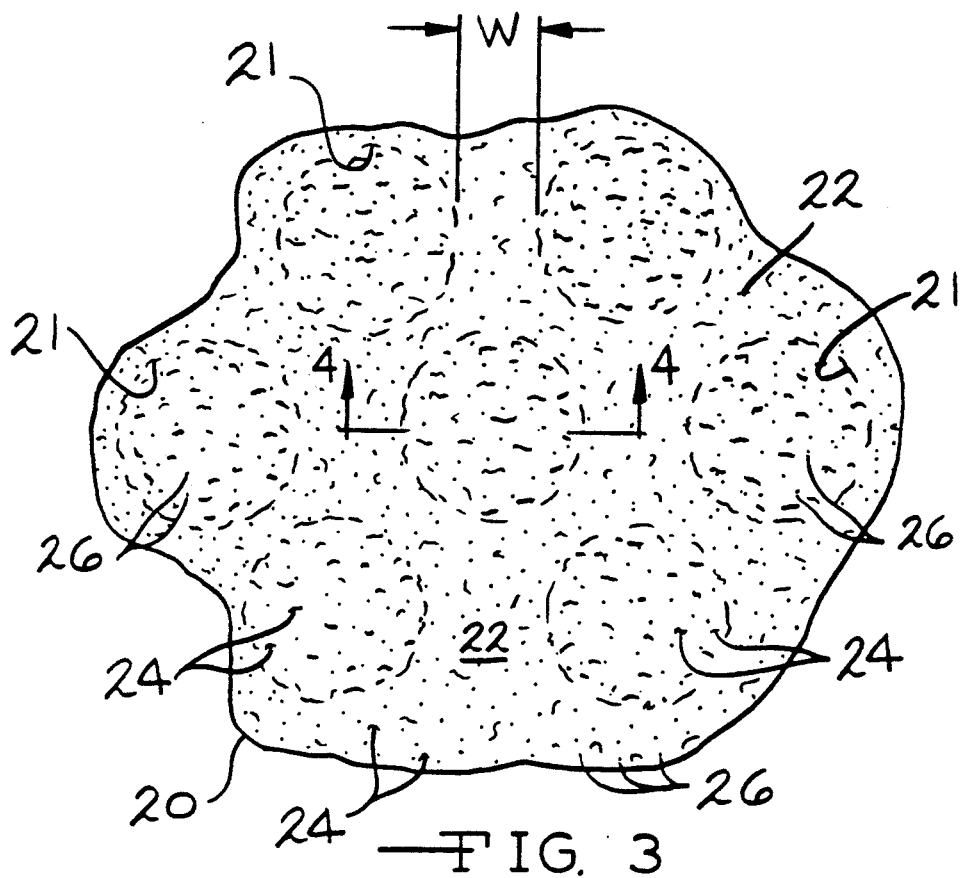
FIG. 3 is a fragmentary plan view of a deep embossed plastic film, according to the present invention.
Figure 4:
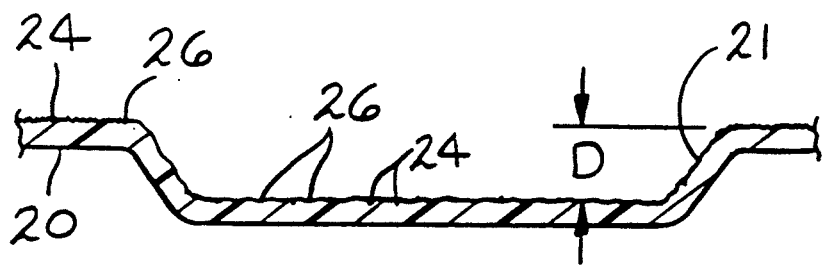
FIG. 4 is an enlarged cross-sectional view taken along the line 4—4 of FIG. 3.

The metal embossing roll 18 may either have a male (protruding) pattern on its outer surface to provide a macro pattern or a female pattern on its outer surface to provide the macro pattern. Referring to FIGS. 3 and 4, the deep embossed plastic film 20 has a plurality of deep embossed macro cells 21. The macro cells 21 are interconnected by lands 22 extending between the adjacent macro cells 21. In the FIG. 3 embodiment, a first plurality of random micro depressions 24 are provided in the areas of the macro cells 21 and the lands 22. In the present embodiment, referring to FIG. 1, the macro cells 21 are provided by female patterns on the metal embossing roll 18. The first plurality of micro patterns 24 are provided by placing a coarse sandblast pattern on the surface of the metal embossing roll 18. In another embodiment, as will be discussed below in connection with the FIG. 2 apparatus, a first set of embossing rollers can be used to produce a micro pattern followed up by a second set of embossing rollers to produce the macro pattern.

As shown in FIG. 4, the depth "D" is preferably between 2.5 mil and 15 mil. The depth "D" of the film 20, shown in FIGS. 3 and 4, is 4 mil.

In the deep embossed plastic film 20, shown in FIGS. 3 and 4, the first plurality of micro depressions 24 are imparted by placing a coarse sandblast pattern on the metal embossing roll 18. It has been found that this coarse sandblast pattern, which results in the random pattern of micro depressions 24, provides an improved tactile quality to the film 20 resulting in a desired "feel" of the final film 20. Preferably, the rough sandblast pattern on the roll 18 falls within a range of 50 to 250 micro inches RA, measured on a perthometer. A preferred range is between 75 and 150 micro inches RA. As discussed above, this sandblast pattern can be placed on the metal embossing roll 18 or on another pair of rolls, such as those shown in FIG. 2.

In the present embodiment, there is a second plurality of micro depressions 26 in the film 20. The second plurality of micro depressions 26 in the present embodiment are randomly placed and are formed by a fine sandblast pattern placed on the metal embossing roll 18. It has been found that the second plurality of micro depressions 26 eliminate the gloss and aid in forming a deep embossed film having an aesthetically pleasing appearance. Preferably, the second plurality of micro depressions 26 are formed by placing a fine sandblasting pattern on the roll 18 having a perthometer measurement of less than 85 micro inches RA and preferably less than 50 micro inches RA. The resilient roll 19, in the present embodiment, is preferably ground to a perthometer range of 35 to 75 micro inches RA.

The film 20 preferably has between 8 and 120 macro cells 21 per inch. More particularly, the embodiment shown in FIG. 3 has 22 macro cells 21 per inch.

As discussed above, the film 20 is constructed by a one-stage process where all three patterns are placed on the metal embossing roll 18. When the film 11 passes between the rolls 18 and 19, the three patterns form the macro cells 21, the first plurality of micro depressions 24 and the second plurality of micro depressions 26.

While the widths vary, in the present embodiment the width "W" of the lands 22 is 0.020 inch. It is understood that the width W varies inversely with respect to the depth "D". Normally, if the metal embossing roll 18 is a male roll, the depths would be deeper, approaching the 15 mil depth. In those situations, the width "W" of the lands 22 is reduced.

Figure 2:
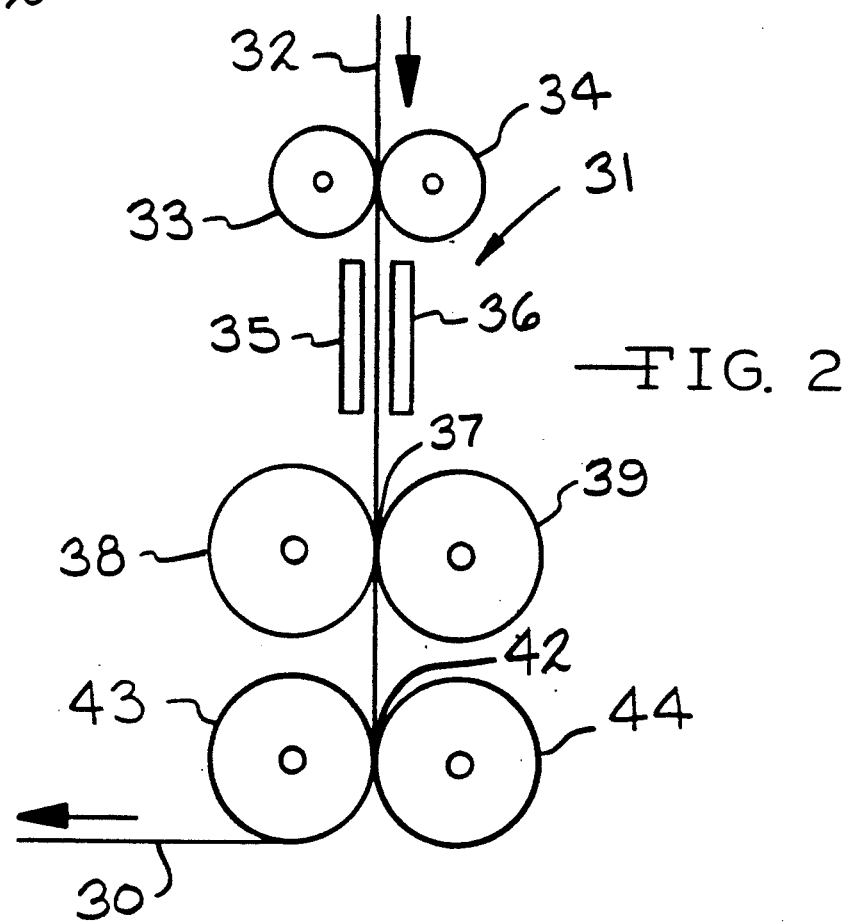
FIG. 2 is a view, similar to FIG. 1, showing another embodiment of apparatus for producing a deep embossed plastic film, according to the present invention.

Referring to FIG. 2, another embodiment of apparatus used to manufacture a deep embossed thermoplastic film 30, according to the present invention, is generally indicated by the reference number 31. A preformed thermoplastic film 32, similar to the film 11 discussed above, is fed through the nip of a pair of pull rolls 33 and 34. The thermoplastic film 32 is then softened by heaters 35 and 36 positioned on opposite sides of the film 32. The heat softened film 32 is then fed through the nip 37 formed by a metal embossing roll 38 and a backup roll 39. The backup roll 39 again has a resilient rubber or rubber-like surface, as discussed above. Next, the film is fed through a nip 42 defined by a second metal embossing roll 43 and a second resilient backup roll 44. The completed deep embossed thermoplastic film 30, according to the present invention, is removed to a windup roll (not shown).

Figure 5:
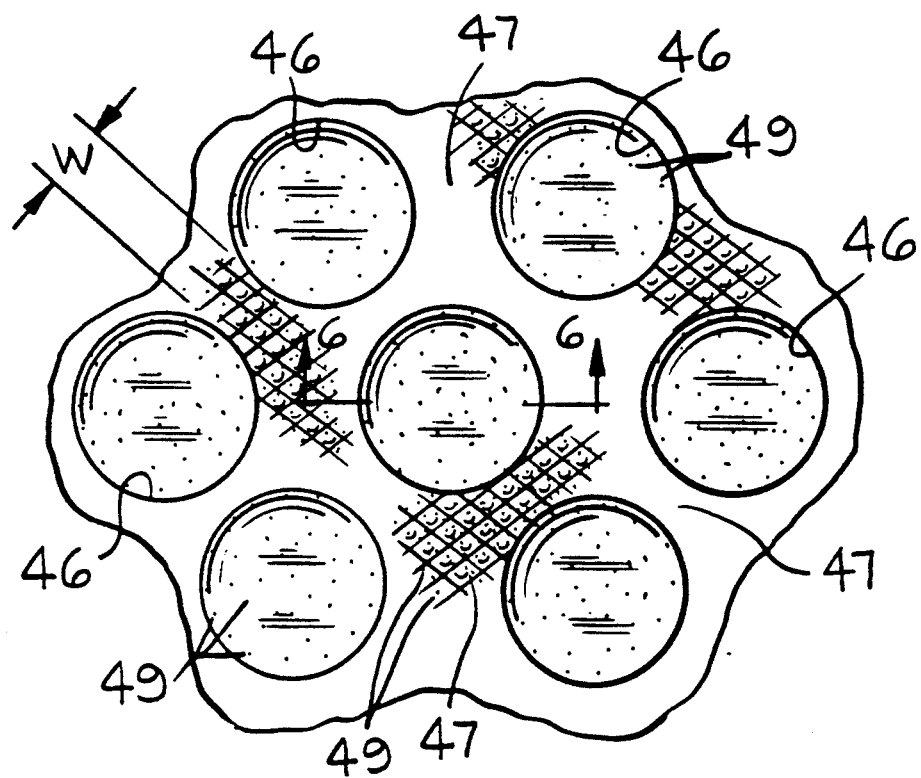
FIG. 5 is a fragmentary plan view, similar to FIG. 3, of another embodiment of deep embossed plastic film, according to the present invention; and, FIG. 6 is an enlarged sectional view taken along the line 6—6 of FIG. 5.
Figure 6:
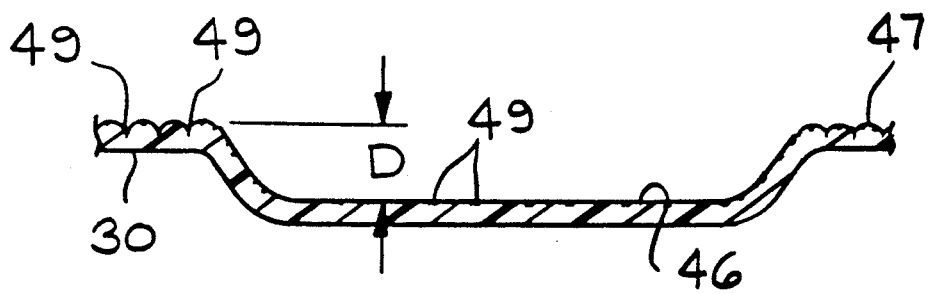

Referring to FIGS. 5 and 6, the deep embossed thermoplastic film 30, according to the present invention, includes a plurality of macro cells 46. Again, there are preferably 8 to 120 macro cells 46 per inch in the film 30. The metal embossing roll 43 may either have a male (protrusion) pattern or a female pattern. The macro cells 46 are formed as the softened thermoplastic film 32 passes between the second pair of rolls 43 and 44. The deep embossed thermoplastic film 30 also includes a first plurality of micro depressions or cells 47. In the present embodiment, the first plurality of micro cells 47 are generally diamond shaped and have a structured pattern, as opposed to the random pattern of the FIG. 3 embodiment. The first plurality of micro cells 47 are formed as the softened film 32 passes between the first pair of rolls 38 and 39. In this embodiment, the diamond shaped pattern is placed on the metal embossing roll 38 to form the diamond shaped micro cells 47. There are approximately 120 to 150 micro cells 47 per inch in the deep embossed thermoplastic film 30.

The macro cells 46 or 21 may have many shapes. The geometry includes triangles, quadrilaterals or increasing multi-sided figures up to and including circles. Similarly, the structured pattern 47 can be patterns other than a diamond pattern and fall within the scope of the present invention.

The diamond shaped micro cells 47 of the deep embossed thermoplastic film 30 provides the tactile quality which, again, results in a proper "feel". The present embodiment also includes a second plurality of random micro cells or depressions 49. The second plurality of random depressions 49 are formed by placing a fine sandblasting pattern on the metal embossing roll 43. As was true in the first embodiment, the sandblast pattern placed on the roll 43 has a preferred perthometer reading of less than 50 micro inches RA. While the structured diamond pattern which forms the micro cells 47 is placed on the upper metal embossing roll 38 and the fine sandblast pattern forming the micro cells 49, together with the macro pattern forming the macro cells 46 both placed on the lower metal embossing roll 43, it should be understood that various ones of the patterns can be moved to the other metal embossing roll 38 or 43 or all three patterns placed on one roll 38 or 43, without departing from the scope of the present invention.

The unembossed film 32 preferably has a thickness between 0.5 mil and 6 mil. The preferred thickness of the film 32 is 1 mil.

The films 20 and 30, according to the present invention, are suitable for use in the disposables field, in agricultural applications and in packaging applications. The films 20 and 30 and other embodiments according to the present invention can specifically be used in diaper back sheets, panty liners, and sanitary napkins.

Many revisions and changes may be made to the specific embodiments disclosed above without departing from the scope of the present invention or from the following claims.

We claim:

1. A deep embossed polyolefin film, said film having a plurality of deep embossed macro cells, said macro cells interconnected by lands extending between adjacent macro cells, said macro cells having a depth of between 2.5 mils and 15 mils, a first plurality of random micro depressions comprising a coarse sandblast pattern, said first plurality of micro depressions having a perthometer range of 50 to 250 micro inches RA, and a second plurality of random micro depressions comprising a fine sandblast pattern, said second plurality of random micro depressions having a perthometer measurement of less than 85 micro inches RA.

2. A deep embossed polyolefin film, according to claim 1, wherein said film includes between 8 and 120 macro cells/inch.

3. A deep embossed thermoplastic film, having a plurality of deep embossed macro cells interconnected by lands extending between adjacent macro cells, said macro cells including a repeating macro cell pattern having a central macro cell surrounded by six spaced macro cells, said macro cells having a depth of between 2.5 mils and 15 mils and at least one plurality of micro depressions provided in addition to said macro cells, said micro depressions having a perthometer range of 35 to 250 micro inches RA.

4. A deep embossed thermoplastic film, having a plurality of deep embossed macro cells interconnected by lands extending between adjacent macro cells, said macro cells having a depth of between 2.5 mils and 15 mils and at least one plurality of micro depressions provided in addition to said macro cells, said micro depressions having a perthometer range of 35 to 250 micro inches RA.

5. A deep embossed thermoplastic film, according to claim 4, wherein said thermoplastic film is a polyolefin film.

6. A deep embossed thermoplastic film, according to claim 4, wherein said micro depressions are provided on said lands.

7. A deep embossed thermoplastic film, according to claim 4, wherein said micro depressions are provided on said lands and in said macro depressions.

8. A deep embossed thermoplastic film, according to claim 4, wherein said thermoplastic film includes two pluralities of micro depressions.

9. A deep embossed thermoplastic film, according to claim 8, wherein a first plurality of micro depressions comprise a coarse sandblast pattern and a second plurality of micro depressions comprise a fine sandblast pattern.

10. A deep embossed thermoplastic film, according to, claim 4, wherein said thermoplastic film includes one plurality of micro depressions comprising a structured pattern.

11. A deep embossed thermoplastic film, according to claim 10, wherein said structured pattern is a diamond pattern.

12. A deep embossed thermoplastic film, according to claim 4, having a second plurality of micro depressions comprising a random sandblast pattern.

13. A deep embossed film, according to claim 1 or 4, wherein said film is used in a diaper back sheet, a panty liner or a sanitary napkin.

* * * * *